United States Patent
Gärber et al.

(10) Patent No.: US 7,711,418 B2
(45) Date of Patent: May 4, 2010

(54) ELECTROIMPEDANCE TOMOGRAPH

(75) Inventors: Yvo Gärber, Lübeck (DE); Markus Steeger, Lübeck (DE); Jianhua Li, Lübeck (DE); Steffen Leonhardt, Lübeck (DE); Jan Rüterbories, Lübeck (DE); Rainer Goldau, Kastorf (DE)

(73) Assignee: Dräger Medical AG & Co. KG, Lübeck (DE)

( * ) Notice: Subject to any disclaimer, the term of this patent is extended or adjusted under 35 U.S.C. 154(b) by 1404 days.

(21) Appl. No.: 10/882,050

(22) Filed: Jun. 30, 2004

(65) Prior Publication Data

US 2005/0059901 A1   Mar. 17, 2005

(30) Foreign Application Priority Data

Aug. 26, 2003   (DE)   ................ 103 39 084

(51) Int. Cl.
  *A61B 5/05*   (2006.01)
(52) U.S. Cl. ........................... 600/547; 128/908
(58) Field of Classification Search ............... 600/547; 607/17, 24; 128/908
  See application file for complete search history.

(56) References Cited

U.S. PATENT DOCUMENTS

| | | | | |
|---|---|---|---|---|
| 4,441,507 A | * | 4/1984 | Steffin | ................ 600/547 |
| 5,025,219 A | | 6/1991 | Gaspard | |
| 5,063,937 A | * | 11/1991 | Ezenwa et al. | ............ 600/536 |
| 5,454,377 A | * | 10/1995 | Dzwonczyk et al. | ....... 600/547 |
| 5,568,144 A | * | 10/1996 | Chiao et al. | ................ 341/139 |
| 5,749,369 A | * | 5/1998 | Rabinovich et al. | ......... 600/547 |
| 6,745,070 B2 | * | 6/2004 | Wexler et al. | ............... 600/547 |

FOREIGN PATENT DOCUMENTS

| | | |
|---|---|---|
| DE | 39 31 395 A1 | 3/1990 |
| EP | 1 000 580 | 5/1700 |
| EP | 0 533 732 B1 | 3/1993 |
| EP | 0 669 822 | 9/1995 |
| WO | WO 94/09699 | 5/1994 |
| WO | WO 98/25519 A1 | 6/1998 |

OTHER PUBLICATIONS

W. Wang et al., 1995, Signal Processing for Noise Equalisation Within EIT Images, The Institution of Electrical Engineers. IEEE, Savoy Place, London WC2R 0BL, UK.

* cited by examiner

*Primary Examiner*—Long V Le
*Assistant Examiner*—Saurel J Selkin
(74) *Attorney, Agent, or Firm*—McGlew and Tuttle, P.C.

(57) ABSTRACT

An electroimpedance tomograph including a plurality of electrodes placed on a body, measuring circuits processing voltage signals recorded by the electrodes, and a control unit supplying two electrodes each with an alternating current. The control unit has a preset feed frequency. The control unit processes the processed voltage signals of all other electrodes to reconstruct the impedance distribution of the body in the electrode plane. The control unit provides for an automatic setting of the current feed frequency/frequencies to record a background frequency spectrum by detecting the electrode voltage signals over a preset period of time and record them as a voltage time series and transform them into a frequency spectrum. The control unit searches in the background frequency spectrum for a frequency (different states) or frequencies (different frequencies) that leads to a useful signal to background ratio above a preset threshold value when used as a feed frequency.

18 Claims, 2 Drawing Sheets

ELECTROIMPEDANCE TOMOGRAPH

CROSS REFERENCE TO RELATED APPLICATIONS

This application claims the benefit of priority under 35 U.S.C. § 119 of German patent application DE 103 39 084.7 filed Aug. 26, 2003 the entire contents of which are incorporated herein by reference.

FIELD OF THE INVENTION

The present invention pertains to an electroimpedance tomograph with a plurality of electrodes that can be placed on the body, electronic circuits that process the voltage signals recorded by the electrodes, and a control unit, which is set up to supply two, preferably adjacent electrodes each with an alternating current, which has a preset feed frequency in case of measurements performed in different states and different preset feed frequencies in case of measurements performed at different frequencies, and to process the processed voltage signals of all other electrodes in order to reconstruct the impedance distribution of the body in the electrode plane from them.

BACKGROUND OF THE INVENTION

Such an electroimpedance tomograph (EIT) is known, for example, from EP 1 000 580 A1, which is used to record an "electroimpedance tomographic image" of a body section of a patient. A corresponding electroimpedance tomography method performed at different frequencies is known from EP 0 669 822 A1.

Electric impedance tomography is a method for the reconstruction of impedance distributions, more precisely, of impedance changes relative to a reference distribution, in electrically conductive bodies. A plurality of electrodes are arranged for this purpose on the conductive surface of the body to be examined, and the control unit, usually a digital signal processor, ensures that a pair of (preferably) adjacent electrodes wherein each is supplied with an alternating electric current (for example, 5 mA at 50 kHz), and the electric voltages are detected at the remaining electrodes and are sent to the control unit. Due to the combination of the measured voltage values during the consecutive rotating current feed, the impedance distribution, more precisely, the change in this distribution compared with a reference distribution, can be reconstructed with suitable algorithms. A ring-shaped equidistant array of 16 electrodes, which can be placed around the body of a patient, for example, with a belt, is used in typical cases. Alternating current is fed into two adjacent electrodes each, and the voltages are measured between the remaining currentless electrode pairs and recorded by the control unit. Due to the rotation of the current feed points, a plurality of measured voltage values are obtained, from which a two-dimensional tomogram of the impedance distribution relative to a reference can be reconstructed in the electrode plane.

Such tomograms are of interest in medicine, because the impedances depend on the biological state of the organs (for example, the state of respiration of the lungs) and/or on the frequency of the current. Both measurements in different states with a given feed frequency and different biological states (for example, observation of the breathing cycles) and measurements performed at different frequencies with different feed frequencies and equal biological state are therefore performed in order to obtain information on the corresponding impedance changes. As was mentioned above, the functional impedance tomography of the lung, in which the electrodes of the EIT are placed around the chest of the patient, is an important application.

An EIT typically comprises a number of electrodes, which can be placed, in particular, on a carrier around the body to be examined in a ring-shaped pattern, and analog electronic circuits for the signal amplification and for the alternating current feed, and digital electronic circuits for digitizing and preprocessing the voltage signals as well as for controlling the current feed, a digital connection with a control unit for controlling the apparatus and for processing the recorded data for the reconstruction of the impedances, as well as a monitor for displaying the impedance distribution. The term "control unit" is used here in a broad sense of this word and it designates a processor unit that both controls the operation of the EIT and performs the evaluation of the detected signals for the reconstruction of the impedance distribution as well as additional analysis operations. A visualization of the reconstructed impedance distribution is then displayed on a monitor.

In prior-art EITs, the frequency (or the frequencies in case of multifrequency measurement) of the feed current is set at the beginning of the measurement manually or by a fixed, stored value and left unchanged, or there is a possibility of changing the frequency of the feed current manually at a later point in time. This procedure is sufficient for laboratory applications, but is unsuitable for the routine operation in medicine, e.g., in intensive care units.

In order to obtain images that can be well reconstructed and interpreted by means of electroimpedance tomography, a high ratio of the useful signal to the interfering signal is necessary. The frequency spectrum of the background (i.e., the sum of all background signals, which lead to voltages at the electrodes) is not known in case of use of an EIT in any space environment, and, moreover, it is usually subject to change over time. Such interfering signals may be caused, for example, by monitors in the environment (ECG, etc.) or other medical apparatus; when other apparatus are switched on at not too great a distance from the EIT, the electromagnetic interferences, and especially the dominant frequencies of these interferences may change. Thus, the ratio of the useful signal to the background may also change in the course of time at a frequency once set at the beginning.

SUMMARY OF THE INVENTION

The object of the present invention is to provide an EIT that is extensively insensitive to electromagnetic background signals without requiring the intervention of a human operator.

The objective of the present invention is achieved by providing an electroimpedance tomograph with a plurality of electrodes that can be placed on a body. Measuring circuits are provided that process the voltage signals recorded by the electrodes. A control unit that is set up to supply two adjacent electrodes with an alternating current that has a preset feed frequency in case of measurements performed under different conditions and at different preset feed frequencies in case of measurements performed at different frequencies. The control unit acts to process the processed voltage signals of all other electrodes in order to reconstruct the impedance distribution of the body in the electrode plane. The control unit is set up for the automatic setting of the current feed frequency/frequencies to record a frequency spectrum or a plurality of frequency spectra of the background by detecting the voltage signals of the electrodes over a preset period of time. The signals are then recorded in the control unit as a voltage time series or a plurality of voltage time series. Subsequently the signals are transformed into a frequency spectrum or frequency spectra. This background frequency spectrum or these background frequency spectra are searched for a frequency (in case of measurements performed in different states) or frequencies (in case of measurements performed at different frequencies) that yields (yield) a useful signal to background signal ratio above a preset threshold value when used as a feed frequency (as feed frequencies).

The objective of the present invention may further be implemented by the electroimpedance tomograph as mentioned above, characterized in that the control unit is set up, furthermore, to automatically repeat the setting of the current feed frequency/frequencies periodically or aperiodically or to repeat it in the presence of preset criteria or to repeat it in a controlled manner by manual input.

The electroimpedance tomograph as mentioned above may have the control unit set up, furthermore, to record the voltage time series without alternating current feed into an electrode pair to determine the frequency spectrum of the background.

The electroimpedance tomograph as mentioned above may have the control unit set up, furthermore, to record the voltage time series with simultaneous alternating current feed to determine the frequency spectrum of the background, wherein the current feed frequency is outside the frequency range of interest, or the voltage time series are determined separately with at least two feed frequencies shifted in relation to one another to such an extent that the signal frequency spectra resulting from these at least two feed frequencies do not overlap.

The electroimpedance tomograph as mentioned above may have the control unit set up, furthermore, to generate a plurality of frequency spectra, which are combined into one frequency spectrum or a plurality of frequency spectra of the background, from the plurality of voltage time series of the electrodes during the automatic determination of the frequency spectrum of the background.

The electroimpedance tomograph as mentioned above may have the control unit set up, furthermore, to generate a warning and to make possible the manual setting of the current feed frequency or to interrupt the EIT measurement if no frequency that leads to a useful signal to background ratio above the preset threshold value when used as a feed frequency/frequencies can be found in the frequency spectrum of the background.

Provisions are made according to the present invention for the control unit to be set up for the automatic setting of the current feed frequency/frequencies. The control unit records for this purpose a frequency spectrum of the background or a plurality of frequency spectra of the background in such a way that the voltage signals of the electrodes are detected over a preset period of time and recorded as a voltage time series in the control unit. This voltage curve over time is then transformed into a frequency spectrum (e.g., by Fourier transformation). The control unit is then set up to search in this background frequency spectrum or in these background frequency spectra for a frequency (in case of measurement in different states) or frequencies (in case of measurements performed at different frequencies) that leads/lead to a useful signal to background signal ratio above a preset threshold value when this frequency/these frequencies is/are used as the feed frequency/frequencies.

A control unit may be programmed, for example, to periodically or aperiodically repeat the automatic setting of the feed frequency or to initiate the automatic setting in the presence of preset criteria or upon a manual command.

Due to the EIT, according to the present invention, no additional external apparatus or instruments need advantageously to be used in order to detect background signals. The electrodes themselves are used, instead, as an "antenna," and the background signals are processed, except for a narrow-band evaluation, in exactly the same manner by the electronic circuits and the control unit, so that the background signals are obtained, thus detected and processed, in such a way as if they were superimposed to the useful signals during the actual measuring operation of the EIT. Due to the transformation of the time course of a time period of the background into a frequency spectrum, it is possible to search for ranges in which the power of the background is sufficiently low, so that a useful signal to background signal ratio above a preset threshold value can be obtained.

In an advantageous embodiment, the frequency spectrum of the background is determined from background signals that are recorded during a time period during which there is no feed of alternating current to an electrode pair. Only the background is recorded in this case, without superimposition by useful signals. As an alternative, it is possible to use a current feed frequency outside the frequency range that is of interest for the EIT measurement operation or consecutively at least two feed frequencies that should, however, be shifted in relation to one another to the extent that the signal frequency spectra resulting from the two different feed frequencies do not overlap.

Provisions are made in an advantageous embodiment for the control unit to generate from the voltage time series of the electrodes a plurality of frequency spectra for the background, which are integrated into a frequency spectrum or a plurality of frequency spectra of the background.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Provisions are made in a preferred embodiment of the EIT with automatic setting of the current feed frequency for the voltage time series to take place for the determination of the background without current feed, i.e., the EIT records the background due to electromagnetic disturbing interfering signals without any superimposition of useful signals. The voltages occurring at the electrodes pass through the analog and digital electric circuits as in the case of normal operation. After digitization of the data with a suitable sampling frequency, a frequency spectrum is determined from the voltage time series in the digital form (by Fourier transformation). The change in the sampling frequency permits, moreover, access to other frequency ranges and/or a change in the lengths of the time periods to be analyzed, which can improve the accuracy of the spectrum. A background frequency spectrum is shown, for example, in FIG. 2. The background spectrum is shown by solid line and it shows, beginning from low frequencies, first a greatly declining shape, which has, toward higher frequencies, a plurality of separate peaks with high interference output, which are indicative of interfering signals with certain frequency ranges.

The resulting measured frequency spectrum, which is generated at a certain set feed frequency during the operation of the EIT, is shown by dotted line. It is seen that the frequency spectrum of the useful signal greatly overlaps here a peak of the background signal, so that a poor useful signal to background signal is obtained. It is also clear that even processing techniques based on the lock-in principle fail to lead to a sufficient suppression of the background in case of great overlap of the frequencies.

Figure 2:
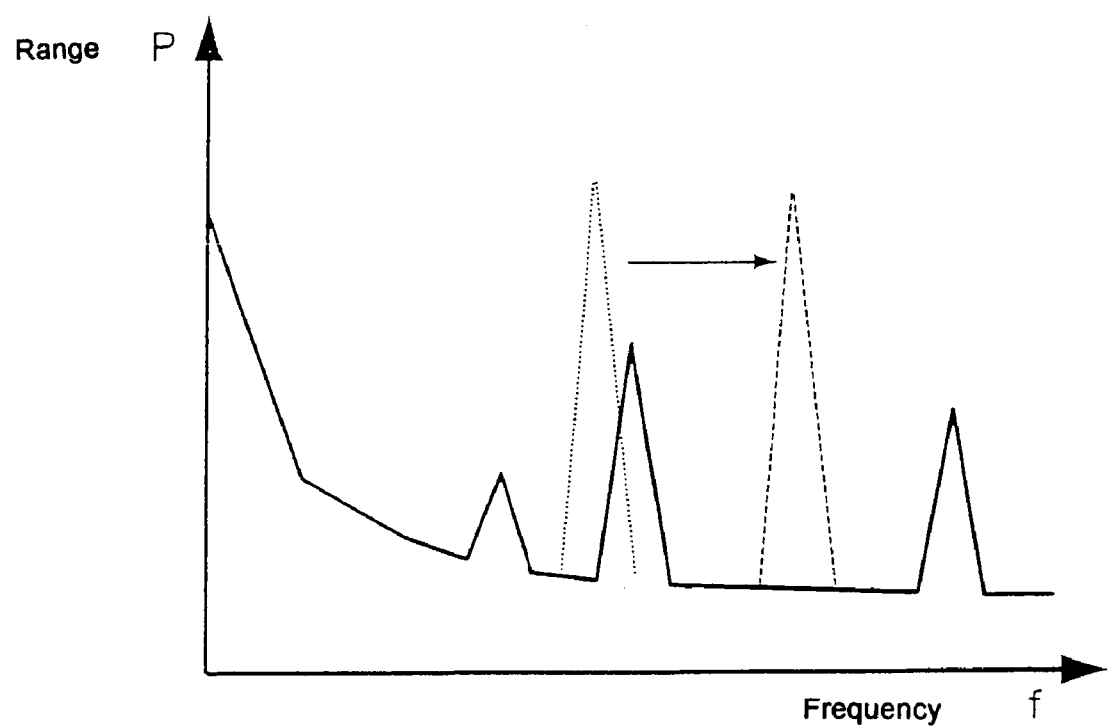
FIG. 2 is a graph illustrating the schematic frequency spectra of the background signal and the useful signal.

The EIT according to the present invention is set up by suitable programming of the control unit such that when a background frequency spectrum as that shown in FIG. 2 is detected, automatic resetting of the current feed frequency is performed, because there is a great overlap with the useful signal frequency spectrum, which is manifested in a low useful signal to interfering signal ratio, in the recorded background spectrum. The EIT according to the present invention is set up by programming the control unit with a suitable algorithm for a search in such a case for a frequency in the background frequency spectrum at which a favorable, i.e., high ratio of the useful signal to the background signal can be obtained. This means, for example, in the view in FIG. 2 that the feed frequency is changed to such a frequency that the frequency curve of the useful signal indicated by broken lines is obtained, and this useful signal is now in a frequency range in which there is relatively little background. The feed frequency found is then stored in the control unit and used during the next measuring operation.

Figure 1:
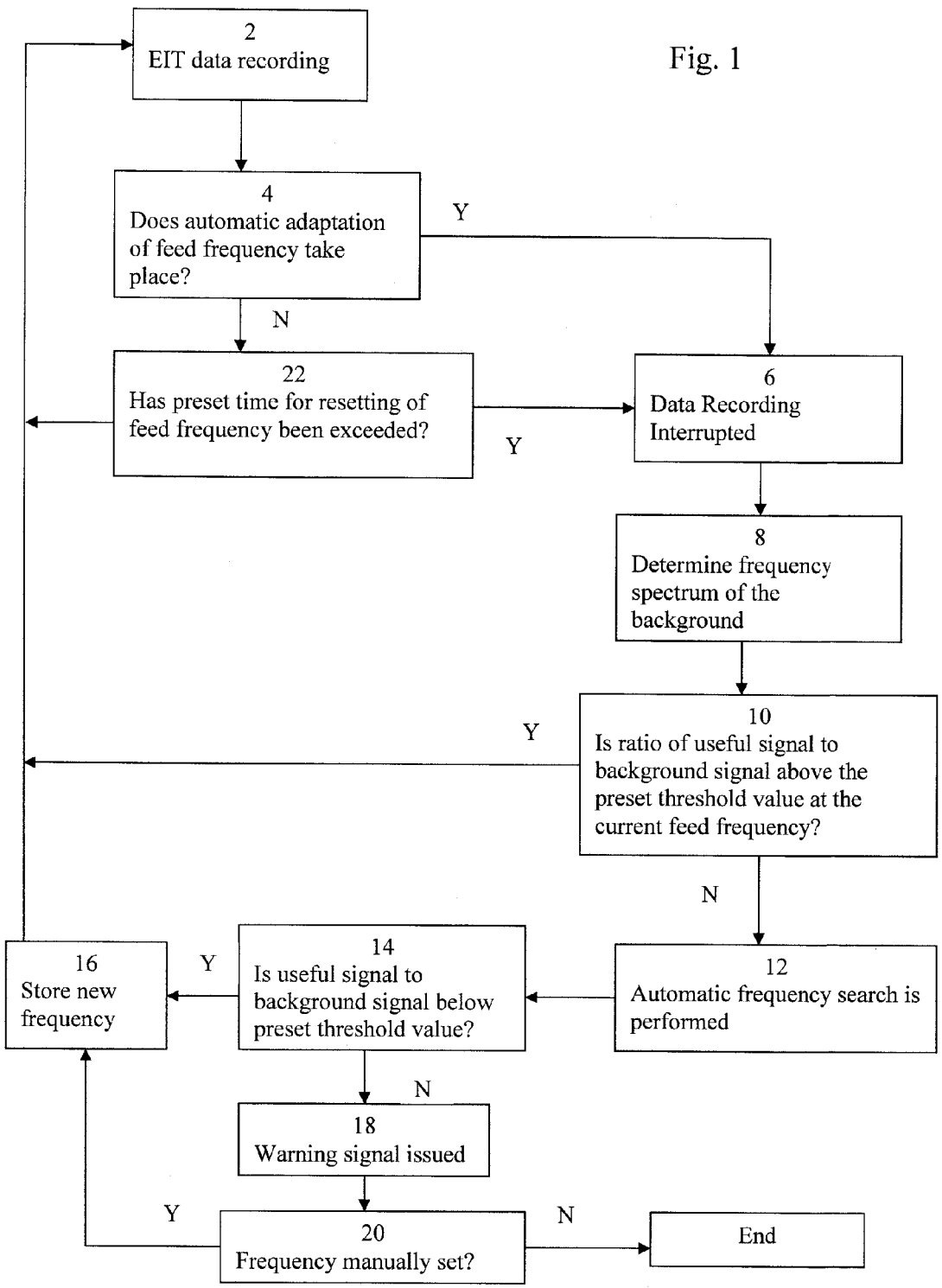
FIG. 1 is a flow chart that illustrates the mode of operation of an EIT according to the present invention.

FIG. 1 shows a possible flow chart to illustrate the mode of operation of the EIT. The apparatus is in block 2 during a phase of the EIT data recording. A poll is performed in the decision block 4 to determine whether an automatic adaptation of the feed frequency shall take place on a manual command, for example, by entry via a keyboard. If such a command is given, or if no such command is given and it is determined in the decision block 22 that a preset time period for the resetting of the feed frequency has been exceeded, the data recording is interrupted in block 6. A frequency spectrum of the background is subsequently determined (block 8), as is schematically shown, for example, in FIG. 2.

It is determined in the decision block 10 whether the ratio of the useful signal to the background signal is above the preset threshold value at the current feed frequency. If the ratio of the useful signal to the interfering signal is above the preset threshold value, the further procedure returns to step 2 for the normal EIT data recording.

If a ratio of the useful signal to the background signal that is below the threshold value is found in the decision block 10, an automatic frequency search is performed in the background spectrum in step 12. If it is determined for the new frequency found during this search in the decision block 14 that the ratio of the useful signal to the background signal is now above the threshold value, the new frequency determined in step 12 is stored in step 16 as a new feed frequency, and the procedure continues with the normal EIT data recording in step 2.

If a useful signal to background signal ratio that is below the preset threshold value is again found for the new frequency in the decision block 14, a warning is sent at first in step 18, and the possibility of a manual frequency setting is subsequently available in block 20, after which the apparatus either returns to step 2 for the normal EIT data recording, or the operation is interrupted.

The setting of the current feed frequency is automatically repeated during the operation of the EIT, and a periodic repetition or an aperiodic repetition may be provided. Furthermore, the control unit may also be set up to repeat the setting of the feed frequency when a preset criterion of conditions is detected by the control unit. It is also possible at any time for a human operator to initiate a new setting of the feed frequency manually, as is shown in FIG. 2.

While a specific embodiment of the invention has been shown and described in detail to illustrate the application of the principles of the invention, it will be understood that the invention may be embodied otherwise without departing from such principles.

What is claimed is:

1. An electroimpedance tomograph comprising:
   a plurality of electrodes configured to be placed on a body;
   measuring circuits that process voltage signals recorded by the electrodes; and
   a control unit supplying two adjacent electrodes with an alternating current having one or more preset feed frequencies, said control unit receiving voltage signals from electrodes not directly supplied with said alternating current such that said control unit reconstructs the impedance distribution of the body in an electrode plane, wherein said control unit automatically sets one or more current frequencies such that said control unit records a frequency spectrum or a plurality of frequency spectra of a background signal based on voltage signals of electrodes received over a preset period of time, said voltage signals being stored in said control unit as a voltage time series, said control unit transforming said voltage time series into a background frequency spectrum, said control unit searching said background frequency for a feed frequency having a useful signal to background signal ratio that is greater than a threshold value, said useful signal having a useful signal frequency range, said background signal having a background frequency range, said threshold value being based on an overlap of said useful signal frequency range with said background frequency range.

2. An electroimpedance tomograph in accordance with claim 1, wherein said control unit automatically repeats said setting of said current feed frequency periodically or aperiodically or to repeat it in the presence of preset criteria or to repeat it in a controlled manner by manual input.

3. An electroimpedance tomograph in accordance with claim 1, wherein said control unit records the voltage time series without alternating current feed into an electrode pair to determine said background frequency spectrum.

4. An electroimpedance tomograph in accordance with claim 1, wherein said control unit records said voltage time series with simultaneous alternating current feed and determines said background frequency spectrum, wherein said current feed frequency is outside a frequency range of interest, or said voltage time series are determined separately with at least two feed frequencies shifted in relation to one another to such an extent that a signal frequency spectra resulting from said at least two feed frequencies do not overlap.

5. An electroimpedance tomograph in accordance with claim 1, wherein said control unit generates a plurality of frequency spectra, which are combined into one frequency spectrum or a plurality of said background frequency spectra, from a plurality of voltage time series of said electrodes during an automatic determination of said background frequency spectrum.

6. An electroimpedance tomograph in accordance with claim 1, wherein said control unit generates a warning and at least allows one of a manual setting of said current feed frequency and interrupting an EIT measurement if no frequency that leads to a useful signal to background ratio above a preset threshold value when used as a feed frequency/frequencies can be found in said background frequency spectrum.

7. A method of recording an electroimpedance tomographic image, the method comprising:
providing a plurality of electrodes configured to be placed on a body;
providing measuring circuits that process voltage signals recorded by the electrodes;
providing a control unit, said control unit supplying two adjacent electrodes with an alternating current that has one or more preset feed frequencies;
processing voltage signals of electrodes not directly supplied with the alternating current;
reconstructing an impedance distribution of the body in an electrode plane, wherein said control unit automatically sets a current feed frequency/frequencies;
recording at least a background frequency spectrum of a frequency spectrum or a plurality of frequency spectra of a background by detecting voltage signals of electrodes over a preset period of time;
recording said voltage signals in said control unit as a voltage time series;
transforming said voltage time series into a frequency spectrum;
selecting at least one feed frequency or feed frequencies based on said background frequency spectrum, said feed frequency or feed frequencies having a useful signal frequency range that has one of no overlap and a minimum overlap with said background frequency spectrum.

8. A method in accordance with claim 7, further comprising: automatically repeating said setting of said current feed frequency any one of
in a controlled manner by manual input;
in the presence of preset criteria;
periodically; and
aperiodically.

9. A method in accordance with claim 7, further comprising:
recording, by said control unit, said voltage time series without alternating current feed into an electrode pair;
determining said background frequency spectrum.

10. A method in accordance with claim 7, further comprising:
with said control unit, recording said voltage time series with simultaneous alternating current feed;
determining said background frequency spectrum, wherein said current feed frequency is outside a frequency range of interest, or said voltage time series are determined separately with at least two feed frequencies shifted in relation to one another to such an extent that a signal frequency spectra resulting from said at least two feed frequencies do not overlap.

11. A method in accordance with claim 7, further comprising:
generating, by said control unit, a plurality of frequency spectra, which are combined into one frequency spectrum from a plurality of voltage time series of said electrodes during an automatic determination of said background frequency spectrum.

12. A method in accordance with claim 7, further comprising: generating, by said control unit, a warning and at least and allowing one of
a manual setting of said current feed frequency and
an interruption in an EIT measurement if no frequency can be found in said background frequency spectrum as a feed frequency/frequencies that leads to a useful signal to background ratio above the preset threshold value.

13. An electroimpedance tomograph comprising:
a plurality of electrodes configured to be placed on a body, said electrodes including sets of two adjacent electrodes and other electrodes;
a measuring circuit means for processing voltage signals received by the electrodes; and
a control unit supplying said sets of two adjacent electrodes with an alternating current that has at least one of a preset feed frequency and different preset feed frequencies, said control unit reconstructing an impedance distribution of the body based on voltage signals received from said other electrodes, said control unit automatically setting a current feed frequency/frequencies, said control unit recording a frequency spectrum or a plurality of frequency spectra of a background signal by detecting voltage signals of said other electrodes over a preset period of time, said voltage signals being recorded in said control unit as a voltage time series, said control unit transforming said voltage time series into a background frequency spectrum, said control unit searching for a frequency or frequencies that yields/yield a useful signal to background signal ratio above a preset threshold value when used as a feed frequency/frequencies based on said background frequency spectrum, said useful signal having a useful signal frequency range, said background signal having a background signal frequency range, said preset threshold value associated with a maximum overlap of said user signal frequency range with said background signal frequency range.

14. An electroimpedance tomograph in accordance with claim 13, wherein said control unit automatically repeats said setting of said current feed frequency any one of
in a controlled manner by manual input;
in the presence of preset criteria;
periodically; and
aperiodically.

15. An electroimpedance tomograph in accordance with claim 13, wherein said control unit records the voltage time series without alternating current feed into an electrode pair to determine said background frequency spectrum.

16. An electroimpedance tomograph in accordance with claim 13, wherein said control unit records said voltage time series with simultaneous alternating current feed and determines said background frequency spectrum, wherein said current feed frequency is outside a frequency range of interest, or said voltage time series are determined separately with at least two feed frequencies shifted in relation to one another to such an extent that a signal frequency spectra resulting from said at least two feed frequencies do not overlap.

17. An electroimpedance tomograph in accordance with claim 13, wherein said control unit generates a plurality of frequency spectra, which are combined into one frequency spectrum or a plurality of said background frequency spectra, from a plurality of voltage time series of said electrodes during an automatic determination of said background frequency spectrum.

18. An electroimpedance tomograph in accordance with claim 13, wherein said control unit generates a warning and at least and allowing one of
a manual setting of said current feed frequency and
an interruption in an EIT measurement if no frequency can be found in said background frequency spectrum as a feed frequency/frequencies that leads to a useful signal to background ratio above the preset threshold value.

* * * * *